United States Patent [19]

Stumpf et al.

[11] 3,963,329

[45] June 15, 1976

[54] SMALL PUPIL BINOCULAR INDIRECT OPHTHALMOSCOPE

[75] Inventors: Joseph G. Stumpf, Fairfield, Conn.; Walter M. Lewis, Wilmette, Ill.

[73] Assignee: Frigitronics of Conn., Inc., Shelton, Conn.

[22] Filed: Aug. 5, 1974

[21] Appl. No.: 494,820

[52] U.S. Cl. .................................... 351/6; 350/145; 351/16
[51] Int. Cl.² ..................... A61B 3/12; G02B 27/02
[58] Field of Search ............... 350/145, 146; 351/6, 351/16

[56] References Cited
UNITED STATES PATENTS
2,757,574    8/1956    Thorburn ........................... 351/6 X
3,582,191    6/1971    Cohen ................................. 351/6 X

*Primary Examiner*—Paul A. Sacher
*Attorney, Agent, or Firm*—Buckles and Bramblett

[57] ABSTRACT

A binocular indirect ophthalmoscope of the type having a central reflecting prism and a pair of adjustable oculars. The instrument may be used in the examination of eyes having either normally dilated or small pupils. Small pupil capability is achieved by making the aperture of each ocular substantially larger than in conventional ophthalmoscopes. By moving the oculars outwardly from the center line of the observer's pupils, the observer views along an axis offset from the optical axis and utilizes the apex portion of the reflecting prism. In this manner, the observer's pupils may be imaged into a patient's pupil as small as 1.5 millimeters in diameter. The plurality of adjustments required in prior art small pupil ophthalmoscopes is thereby avoided.

The foregoing abstract is not to be taken either as a complete exposition or as a limitation of the present invention. In order to understand the full nature and extent of the technical disclosure of this application, reference must be had to the following detailed description and the accompanying drawings as well as to the claims.

6 Claims, 11 Drawing Figures

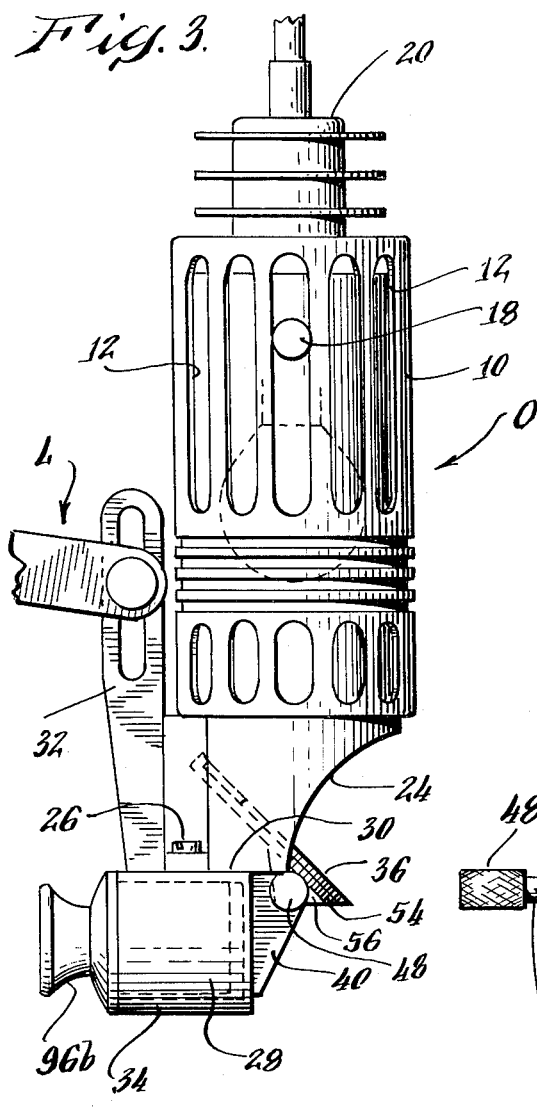
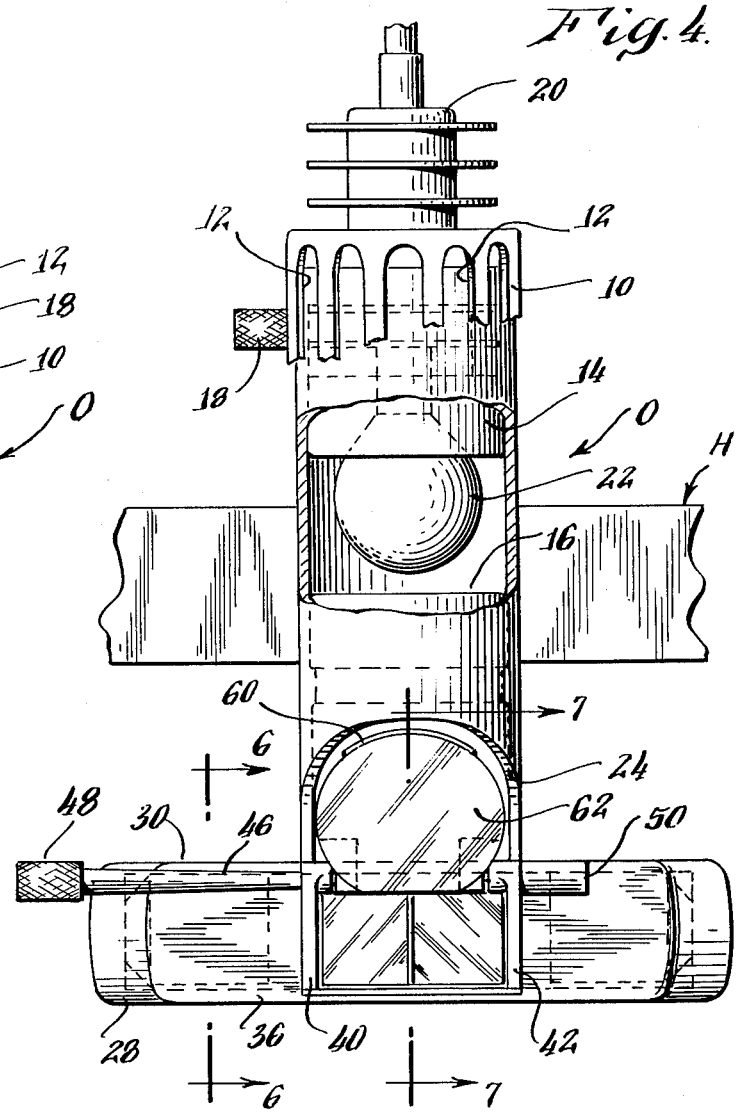
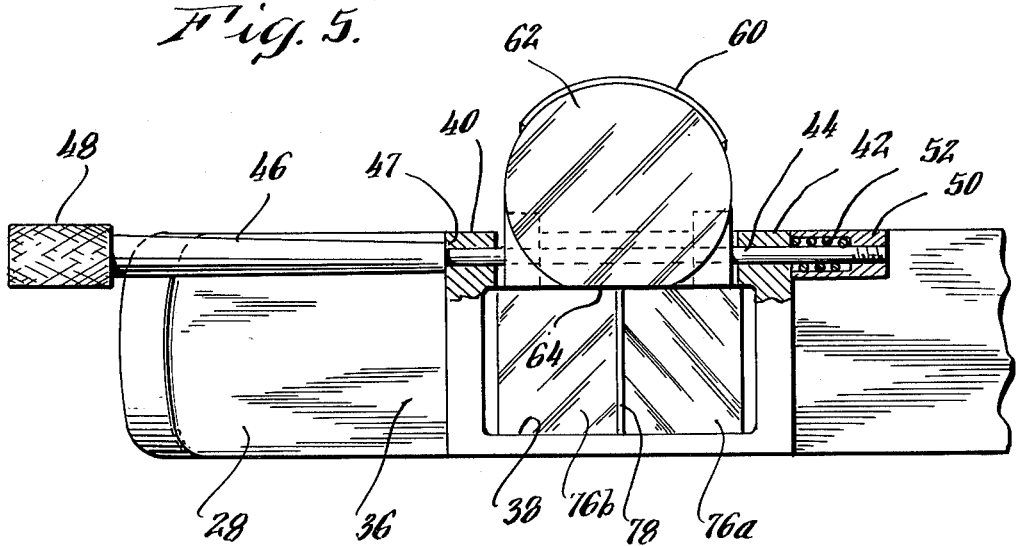

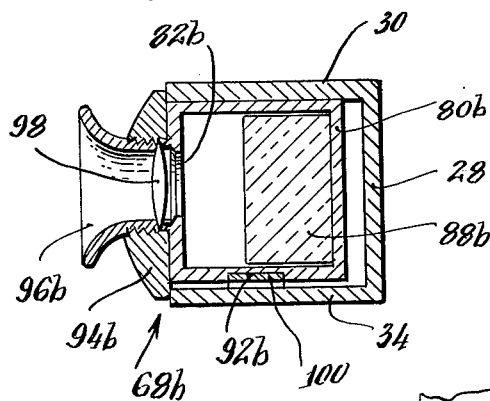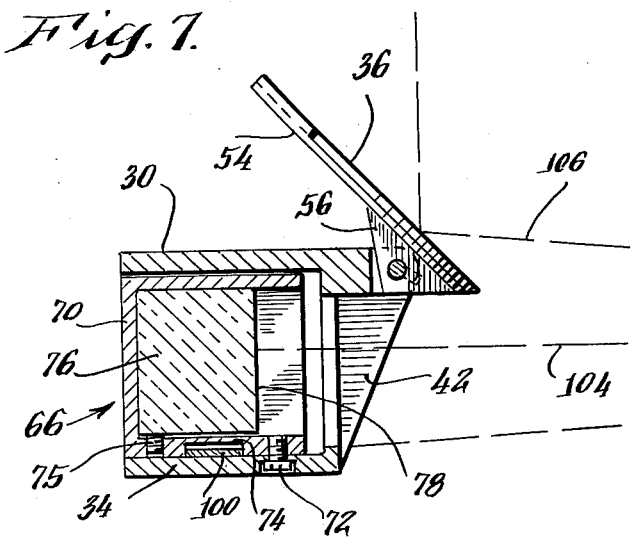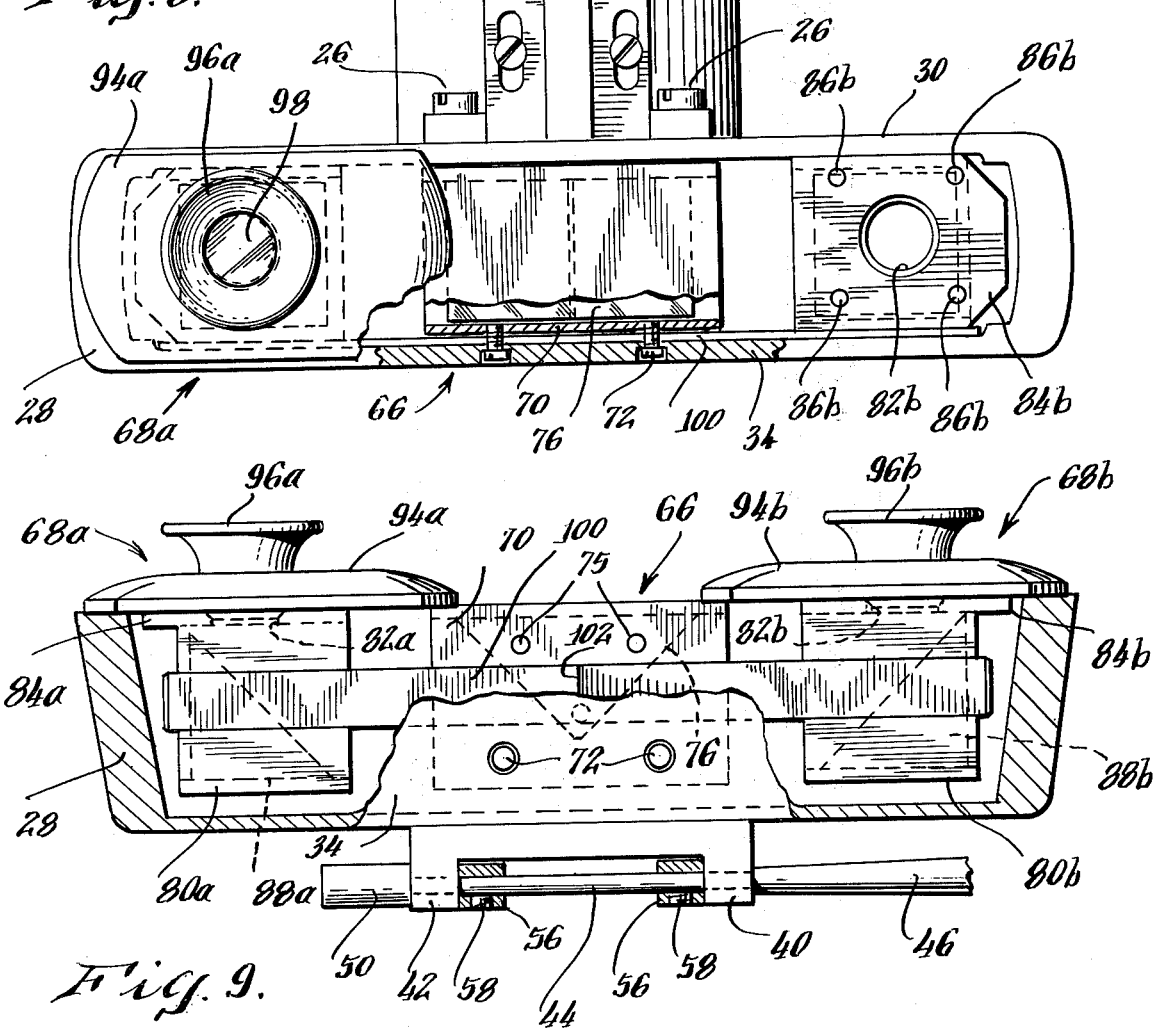

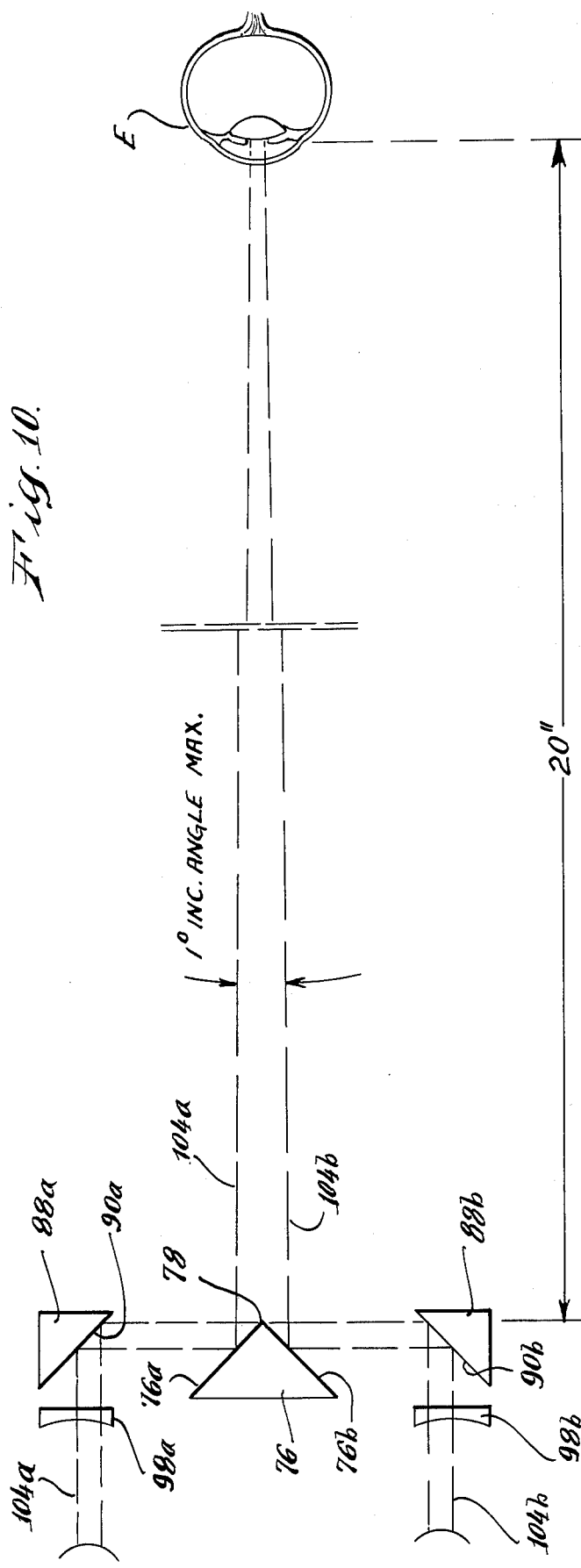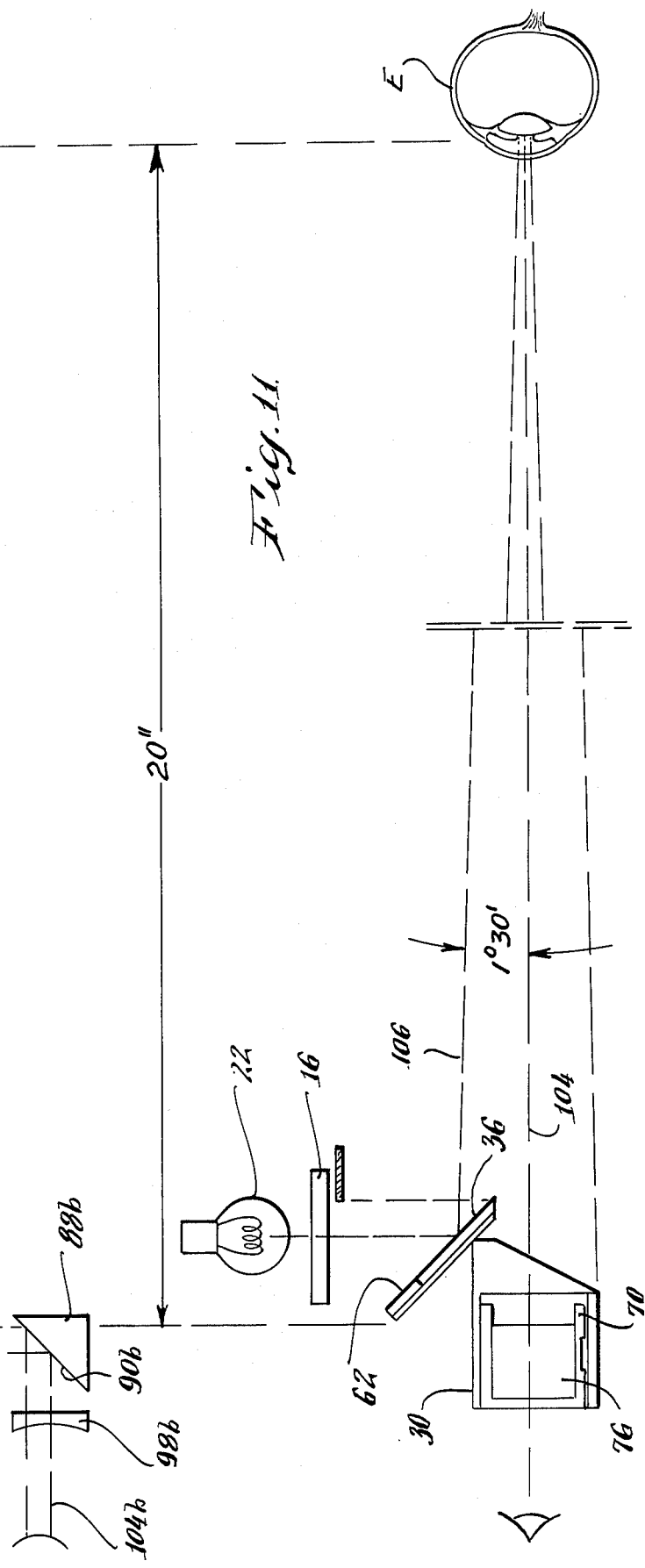

3,963,329

SMALL PUPIL BINOCULAR INDIRECT OPHTHALMOSCOPE

BACKGROUND OF THE INVENTION

This invention pertains to binocular indirect ophthalmoscopes and, more particularly, to such an ophthalmoscope having small pupil capability but without the several adjustments required in prior art ophthalmoscopes of this nature.

For optimum binocular ophthalmoscopy, three inverted images should be formed in the patient's pupil. These are the observer's two pupils and the light source. This is pointed out in an article entitled "Clinical Evaluation of the Small Pupil Binocular Indirect Ophthalmoscope," by Horland, Elzeneiny, and Schepens appearing in Vol. 82, Archives of Ophthalmology, Oct. 1969, at pages 466–474. It is also important that the three images be separated as much as possible. The images of the observer's pupils should be separated in order to provide maximum stereopsis. The light source image must be separated from the pupil images in order to minimize reflections from the cornea and the crystalline lens. A number of prior art ophthalmoscopes are capable of such results when viewing the fundus through a normally dilated pupil. However, approximately one per cent (1%) of patients have pupils which do not dilate or have other conditions resulting in partial obscuration of the pupil. In order to properly examine these patients, small pupil ophthalmoscopes have been employed.

The previously cited article in the Archives of Ophthalmology discloses a small pupil ophthalmoscope which may be employed in pupils as small as 1.5 millimeters while retaining stereopsis and reducing reflection. However, a number of adjustments are required of the user in making examinations through a small pupil. First, of course, there is the usual adjustment for the interpupillary distance (PD) of the observer. In addition, three adjustable mirrors are provided — one for the light source and one for each of the observer's pupils. As a result of the several additional adjustments required for use as a small pupil instrument, the ophthalmoscope is more complex and expensive than is desirable. Accordingly, it is the primary object of the present invention to provide a binocular indirect ophthalmoscope which is capable of examination through small pupils but does not require the additional adjustments of prior art instruments. Another object is to provide such an instrument which retains optimum stereopsis and minimum reflection. Other objects, features, and advantages will be apparent from the following description and appended claims.

SUMMARY OF THE INVENTION

The invention is an improvement in binocular indirect ophthalmoscopes. Such ophthalmoscopes conventionally include a horizontal mirror housing surmounted by a vertical lamp housing, and a lamp and condensing lens within the lamp housing, a mirror for directing light from the lamp into a patient's eye, and a V-shaped side-splitting mirror centrally positioned in the mirror housing having first and second reflective surfaces for receiving light reflected from the patient's eye and directing it toward opposite ends of the mirror housing. Left and right ocular assemblies are adjustably mounted in the mirror housing, each including a member defining an aperture for a user's eye and an angled mirror for directing light from a respective one of the reflective surfaces through the aperture. The improvement of this invention resides in the fact that the aperture of each ocular assembly is made sufficiently large that the assemblies may be moved apart to a distance substantially greater than the user's interpupillary distance. For example, the apertures of this invention may be as large as 9/16 inch diameter, as opposed to conventional apertures as small as one-forth inch. This enables the user's eyes to receive radiation from portions of the first and second reflective surfaces which are immediately adjacent the apex of the side-splitting mirror and thereby permit eye examination through a small pupil.

BRIEF DESCRIPTION OF THE DRAWINGS

FIG. 3 is a side view of the ophthalmoscope of this invention;

FIG. 4 is a front view of the ophthalmoscope of FIG. 3, partially broken away to illustrate its internal construction;

FIG. 5 is an enlarged front view of a portion of the ophthalmoscope of FIG. 4;

FIG. 6 is an enlarged cross section taken substantially along the line 6—6 of FIG. 4;

FIG. 7 is an enlarged cross section taken substantially along the line 7—7 of FIG. 4;

FIG. 8 is a view of a portion of the ophthalmoscope as seen from the user's position, portions thereof being broken away to illustrate its internal construction;

FIG. 9 is a bottom view of the ophthalmoscope of FIG. 8, portions thereof being broken away to illustrate its internal construction;

FIG. 10 is a top schematic view illustrating the ocular optics of this invention; and FIG. 11 is a side schematic view illustrating the relationship between the ocular and illumination optics of this invention.

DESCRIPTION OF THE PREFERRED EMBODIMENT

Figure 1:
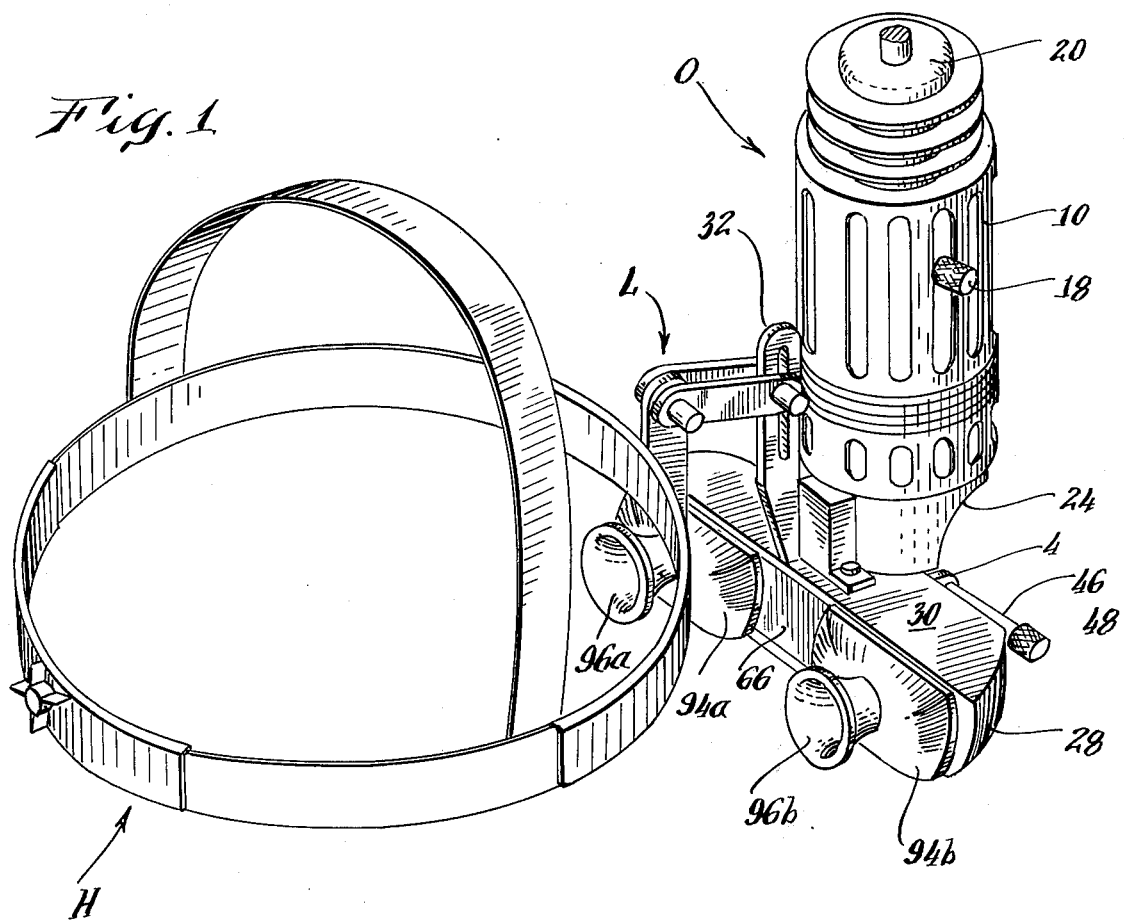
FIG. 1 is a perspective view of an ophthalmoscope embodying this invention.
Figure 2:
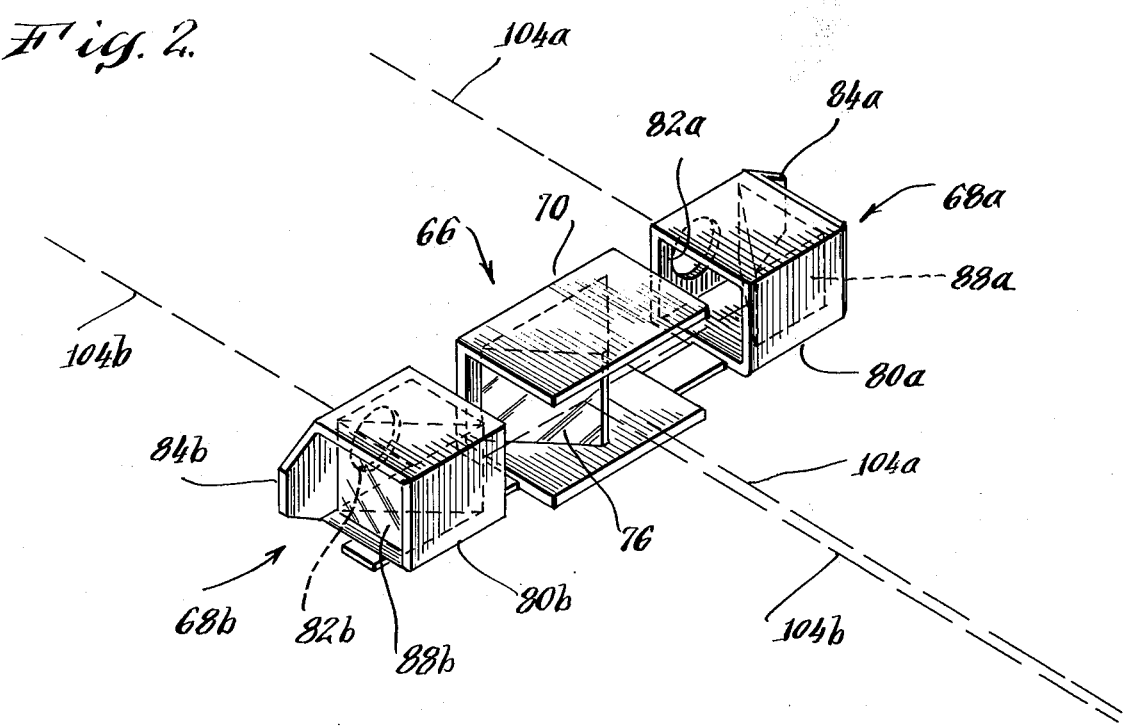
FIG. 2 is a perspective view of the central mirror and ocular assemblies, removed from their housing for purposes of illustration.

With particular reference to FIG. 1 there is illustrated an ophthalmoscope O in accordance with this invention secured to a conventional headband H by means of a conventional link assembly L. The ophthalmoscope is illustrated in more detail in FIGS. 3 and 4. It comprises a substantially cylindrical vertical lamp housing 10 having ventilation openings 12 surrounding a lamp sleeve 14 which carries therein a condensing lens assembly 16. Adjustably mounted in the top of sleeve 14 by means of a set screw 18 is a finned lamp base 20 and lamp 22. The lower end of sleeve 14 defines a cutout 24 facing in the direction of the patient. Secured to the bottom of the sleeve by means of screws 26 is a substantially rectangular horizontal mirror housing 28.

The mirror housing 28 includes a solid top wall 30 from which extends a vertical mounting bracket 32 and a solid bottom wall 34. Its front wall 36 defines a rectangular central opening 38 while the back of the mirror housing is open. A pair of spaced flanges 40, 42 are positioned at either side of front opening 38. Supported within the flanges 40, 42 is a mirror support pin 44.

Support pin 44 has an enlarged portion 46 defining a shoulder 47 which engages flange 40. The left end of pin 44 terminates in a knurled mirror adjusting knob 48. At its right end, as viewed in FIG. 5, the threaded end of support pin 44 is engaged by a hollow nut 50 enclosing a compressed coil spring 52. An illuminating mirror base plate 54 includes a pair of spaced shoulders 56 (FIGS. 7, 9) through which the support pin 44 passes and to which it is secured by means of set screws 58 (FIG. 9). As will be seen by particular reference to FIG. 5, the base plate 54 is rectangular at its lower edge and circular at its upper edge. The upper circular edge has a raised semi-circular lip 60 and cemented against the lip 60 is a circular illuminating mirror 62. The lower edge 64 of mirror 62 is squared off to match the edge of base plate 54. The mirror 62 is positioned below and forward from the position of illuminating mirrors in conventional ophthalmoscopes to reduce reflections as will be explained below.

Positioned within the hollow mirror housing 28 are a central prism assembly 66, a left ocular assembly 68a, and a right ocular assembly 68b. The prism assembly 66 comprises a channel shaped prism mount 70 having its open side facing the opening 38 in the mirror housing and secured in place by means of screws 72. The bottom surface of the mount 70 defines an elongated slot 74 (FIG. 7) running parallel with mirror housing 28. Positioned within the mount 70 by screws 75 is a solid triangular side-splitting prism 76 having reflective surfaces 76a, 76b meeting at an apex 78.

The left and right ocular assemblies, 68a, 68b respectively, are substantially identical, although mirror images of each other. Accordingly, the elements thereof will be given similar reference numerals but with either an *a* or *b* appended. Each ocular assembly includes a metallic prism box 80 in the form of an open-ended tube of square cross section. The open ends of the prism boxes are aligned parallel with the mirror housing 28 and the rear wall (that facing the user) defines an aperture 82. An extension of the back wall forms a tab 84 adjacent the end of the mirror housing 28 and also includes four tapped screw holes 86 spaced around the aperture 82. Secured within the box 80, and fixed relative to aperture 82 is a solid triangular prism 88 having a 45° reflective surface 90 positioned to direct radiation from the central prism 76 through the aperture 82. The bottom wall of each of the boxes 80 defines a slot 92 (FIG. 6). Secured to the rear wall of each of the prism boxes 80 by means of screws engaging the threaded holes 86 is a substantially rectangular eyelet housing 94 enclosing the open side of mirror housing 28 and having a threaded opening into which is screwed an eyelet 96 which secures a relatively weak lens 98 over the aperture 82.

The ocular assemblies are maintained within the mirror housing 28 and in sliding relation thereto by means of a leaf spring 100. The leaf spring 100 is normally slightly V-shaped with its apex 102 centrally positioned within the mirror housing 28, the spring lying within the slot 74 in the bottom of mirror mount 70. The free ends of the spring 100 lie within the slots 92a, 92b of the prism boxes, forcing them upward and into frictional sliding engagement with the top wall 30 of the mirror housing 28.

The operation of the ophthalmoscope of this invention will now be described with particular reference to FIGS. 10 and 11 which schematically illustrate an ophthalmoscope as described herein employed in the examination of a patient's eye having a small pupil and at an average range of 20 inches. The optical axes of the instrument are shown as 104a and b. The angle at apex 78 of prism 76 is slightly greater than 90°, causing the axes to define a maximum included angle of 1°. For stereoscopic viewing of an eye with a normally dilated pupil, these axes would also be the optical axes of the observer's eyes, and accordingly, the user's eyes would be reflected from surfaces 76a, 76b of central prism 76 centered about such axis. However, should the user encounter a small pupil, the only adjustment required is to slide the ocular assemblies outwardly so that they are spaced apart a distance somewhat greater than the observer's interpupillary distance. As shown in FIG. 10, those portions of reflective surfaces 76a, 76b 76b immediately adjacent apex 78 will now be employed and the observer's pupils will, in effect, be imaged within the pupil of the examined eye. This construction simplifies the construction and operation of the instrument as no angular adjustment of prisms 88a, b is required. Each mirror remains fixed relative to its aperture.

It is also important to minimize any reflection of the illuminating lamp from the cornea or lenticular surfaces while still imaging the illuminating lamp 22 within the small pupil. As shown in FIG. 11 this is accomplished in the present invention by positioning lamp 22 forwardly from the usual position and positioning the mirror 62 very closely adjacent the central prism 76. The light axis 106 forms an angle with the optical axes 104 which does not exceed 2° and has an optimum value of 1°30′. It is not necessary that illuminating mirror 62 be adjustable. It might be formed, for example, as a third reflecting surface of prism 76. The function of the lip 60 is to prevent stray light from entering the instrument through the edge of mirror 62. The bottom edge of the mirror is painted black for the same reason.

It is believed that the many advantages of this invention will now be apparent to those skilled in the art. For example, the ophthalmoscope may be employed for conventional examination but is readily adaptable to viewing a small pupil by simply sliding the ocular assemblies apart until they are spaced slightly greater than the interpupillary distance of the user. The lenses 98 are relatively weak and may be, for example, approximately 2× power. As a result little distortion is created even when viewing off-axis. It will also be apparent that a number of variations and modifications may be made in this invention without departing from its spirit and scope. Accordingly, the foregoing is to be construed as illustrative only, rather than limiting. This invention is limited only by the scope of the following claims.

We claim:

1. In a binocular indirect ophthalmoscope of the type having a horizontal mirror housing surmounted by a vertical lamp housing, a light source within the lamp housing, an illuminating mirror for directing light from the source into a patient's eye, V-shaped side-splitting mirror means centrally positioned in said mirror housing having first and second angled reflective surfaces for receiving light reflected from the patient's eye and directing it toward opposite ends of said mirror housing, and left and right ocular assemblies adjustably mounted in said mirror housing, each of said assemblies including a member defining an aperture for a user's eye and an angled mirror for directing light from a respective one of said reflective surfaces through said aperture, the improvement which comprises: the left and right optical axes between the side-splitting mirror means and a patient's eye including a maximum angle of 1°; the optical axis of the light source and the plane of the left and right optical axes of the ocular assemblies defining a maximum included angle of substantially 2°, measured between the ophthalmoscope and a patient's eye; and said ocular assemblies being sufficiently movable within said mirror housing that said assemblies are adjustable between a first location separated by a distance substantially equal to the user's interpupillary distance and a second location separated by a distance substantially greater than the same user's interpupillary distance, enabling the user's eyes to receive light from portions of said first and second reflective surfaces immediately adjacent the apex of said side-splitting mirror, thereby permitting eye examination through a substantially undilated pupil.

2. The improvement of claim 1 wherein the aperture and mirror of each ocular assembly are fixed relative to one another.

3. The improvement of claim 1 wherein the included angle between the optical axis of the light source and the plane of the left and right optical axes of the ocular assemblies is substantially 1°30', measured between the ophthalmoscope and a patient's eye.

4. The improvement of claim 1 wherein said mirror housing includes means for resiliently biasing each of said ocular assemblies into frictional sliding engagement with a wall of said mirror housing.

5. The improvement of claim 4 wherein said biasing means comprises a leaf spring.

6. The improvement of claim 1 wherein said illuminating mirror includes means for adjusting its angular inclination.

* * * * *